(12) United States Patent
Reissner et al.

(10) Patent No.: US 11,497,938 B1
(45) Date of Patent: *Nov. 15, 2022

(54) SYSTEM AND METHOD FOR GENERAL DATA PROTECTION REGULATION (GDPR) COMPLIANT HASHING IN BLOCKCHAIN LEDGERS

(71) Applicant: Syniverse Technologies, LLC, Tampa, FL (US)

(72) Inventors: Guido Reissner, Udenheim (DE); Monique Jeanne Morrow, Zurich (CH)

(73) Assignee: Syniverse Technologies, LLC, Tampa, FL (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/024,017

(22) Filed: Sep. 17, 2020

Related U.S. Application Data

(63) Continuation of application No. 16/737,216, filed on Jan. 8, 2020, now Pat. No. 10,812,455.

(60) Provisional application No. 62/925,546, filed on Oct. 24, 2019.

(51) Int. Cl.
| | | |
|---|---|---|
| *H04L 29/06* | (2006.01) | |
| *A61N 5/10* | (2006.01) | |
| *C04B 35/645* | (2006.01) | |
| *G21K 5/04* | (2006.01) | |
| *C04B 35/553* | (2006.01) | |
| *G21G 4/02* | (2006.01) | |

(52) U.S. Cl.
CPC ......... *A61N 5/1077* (2013.01); *A61N 5/1042* (2013.01); *C04B 35/553* (2013.01); *C04B 35/645* (2013.01); *C04B 35/6455* (2013.01); *G21G 4/02* (2013.01); *G21K 5/04* (2013.01); *A61N 2005/109* (2013.01); *A61N 2005/1094* (2013.01); *A61N 2005/1095* (2013.01)

(58) Field of Classification Search
CPC ................ A61N 5/1077; A61N 5/1042; A61N 2005/109; A61N 2005/1094; A61N 2005/1095; C04B 35/553; C04B 35/645; C04B 35/6455; G21G 4/02; G21K 5/04
USPC .......................................................... 713/153
See application file for complete search history.

(56) References Cited

U.S. PATENT DOCUMENTS

2002/0186837 A1* 12/2002 Hopkins ............... H04L 9/3033
380/28
2019/0116142 A1* 4/2019 Chalakudi ............ H04L 67/104

* cited by examiner

*Primary Examiner* — Evans Desrosiers
(74) *Attorney, Agent, or Firm* — Molly L. Sauter; Smith & Hopen, P.A.

(57) ABSTRACT

A computer implemented system and method for providing general data protection regulation (GDPR) compliant hashing in blockchain ledgers. The invention guarantees a user's right to be forgotten, in compliance with the GDPR regulations, utilizing blockchain technologies.

17 Claims, 4 Drawing Sheets

SYSTEM AND METHOD FOR GENERAL DATA PROTECTION REGULATION (GDPR) COMPLIANT HASHING IN BLOCKCHAIN LEDGERS

CROSS-REFERENCE TO RELATED APPLICATIONS

This application claims priority to currently pending U.S. patent application Ser. No. 16/737,216, filed on Jan. 8, 2020 and entitled, "System and Method for General Data Protection Regulation (GDPR) Compliant Hashing in Blockchain Ledgers", which claims prior to U.S. Provisional Patent Application No. 62/925,546, filed on Oct. 24, 2019 and entitled, "System and Method for General Data Protection Regulation (GDPR) Compliant Hashing in Blockchain Ledgers", the entirety of which are both incorporated herein by reference.

TECHNICAL FIELD

The present invention relates to computer architectures and methods that automatically comply with data security regulations using immutable audit ledgers, such as blockchains. In particular, the invention provides a computer system and method that effectively complies with data processing regulations, including, but not limited to, the European Union's General Data Protection Regulation (GDPR).

BACKGROUND OF THE INVENTION

In accordance with GDPR, Personal Identifiable Information (PII), such as an individual's name, phone number, address, etc. are protected by law and these laws often include the so-called "right to be forgotten". In most of the current blockchain technologies, one cannot delete information from a blockchain ledger because it is tamper-proof. However, in certain geographical regions having GDPR laws, the inability to delete PII stored in a blockchain ledger may lead to a violation of these data privacy laws, and in particular, a violation of the right to be forgotten.

In general, personally identifiable information (PII) is any data that can be used to identify a specific individual. Social Security numbers, mailing or email address, and phone numbers have most commonly been considered PII. However, PII may also include an IP address, login IDs, social media posts, or digital images. Geolocation, biometric, and behavioral data can also be classified as PII.

A common mitigating solution to complying with GDPR laws is to store a) hash value, rather than the actual personal data (message), in the blockchain ledger, which makes it difficult to reconstruct the original personal data, especially if the message is padded prior to hashing. However, storing only the hash values of the personal data may not be enough, because it is still possible to draw conclusions on the personal data based upon the stored hash value and as such the personal data is not considered to have been deleted from the blockchain ledger. For example, knowing the hash function used for a given message m, it is possible for one to exhaust, by brute force, the padding space and see which hash values v are obtained in this way because, if a given hash v is not obtained then it can be concluded that m was not the message. For example, a hash value may be mapped to data of any size and together with cryptographic functionality can be used to confirm a data fingerprint (SHA-1, SHA-256. MD-5 etc.). While prior art methods are known which utilize a Merkle Tree function to generate the hash value, the resulting "hash" is still a data point and therefore can be challenged with GDPR compliance. As such, in order to be GDPR compliant, a hash value must not be attributed to the PII and must be proven as such.

Additionally, assuming that personal identifiable information (PII) is encrypted rather than hashed before it is written to a blockchain, destroying the cryptographic key renders the stored data unreadable. However, again it is still possible to draw conclusions based on the encrypted message by exhausting the cryptographic keys. As a result, one could launch a challenge against an enterprise employing blockchain technology as to whether or not the enterprise is in compliance with GDPR.

Accordingly, there is a strong but, heretofore, unresolved need in the art for a system and method for ensuring GDPR compliance by enterprises that utilize blockchain technology.

SUMMARY OF THE INVENTION

In various embodiments, the present invention provides a system and method employing a new family of hash functions, rather than a single function, that obviates instantiation of data between source and destination that results in a new hash value which does not include information on the original data.

In one embodiment, the present invention provides a computer implemented method for providing general data protection regulation (GDPR) compliant hashing in blockchain ledgers. The method includes, receiving a first message from a user at a blockchain gateway device, wherein the first message comprises personal identification information (PII) and performing, at the blockchain gateway device, a first hashing function on the first message to obtain a hash value of the first message. The method further includes, storing the hash value of the first message in a blockchain ledger, storing the first hashing function in an off-chain database and storing the first message in the off-chain database.

When a user of the blockchain desires to be forgotten, the method further includes, receiving a request to delete the first message, arbitrarily selecting a second message that is different than the first message and calculating a second hashing function using the second message, wherein the second hashing function results in the same hash value. The method further includes, replacing the first message in the off-chain database with the second message and replacing the first hashing function in the off-chain database with the second hashing function.

In an additional embodiment, the present invention provides a blockchain gateway device for providing general data protection regulation (GDPR) compliant hashing in blockchain ledgers. The blockchain gateway device includes, a processor and one or more memory devices storing computer-executable instructions that, when executed with the processor, cause the system to at least, receive a first message from a user, wherein the first message comprises personal identification information (PII) and perform a first hashing function on the first message to obtain a hash value of the first message. The device is further configured to store the hash value of the first message in a blockchain ledger, store the first hashing function in an off-chain database and store the first message in the off-chain database. The blockchain gateway device is further configured to receive a request to delete the first message, arbitrarily select a second message that is different than the first message, calculate a second hashing function using the second message, wherein the second hashing function results in the same hash value, replace the first message in the off-chain database with the second message and replace the first hashing function in the off-chain database with the second hashing function.

In an additional embodiment, the present invention provides one or more non-transitory computer-readable media having computer-executable instructions for performing a method of running a software program on a computing device for providing general data protection regulation (GDPR) compliant hashing in blockchain ledgers.

In the present invention, the personal identification information (PII) of the user may include one or more of, social security numbers, mailing addresses, email addresses, phone numbers, IP addresses, login IDs, social media posts, digital images, geolocation data, biometric data, and behavioral data.

Accordingly, in various embodiments, the present invention provides a system and method for ensuring GDPR compliance by enterprises that utilize blockchain technology.

BRIEF DESCRIPTION OF THE DRAWINGS

For a fuller understanding of the invention, reference should be made to the following detailed disclosure, taken in connection with the accompanying drawings, in which.

DETAILED DESCRIPTION OF THE INVENTION

Figure 1:
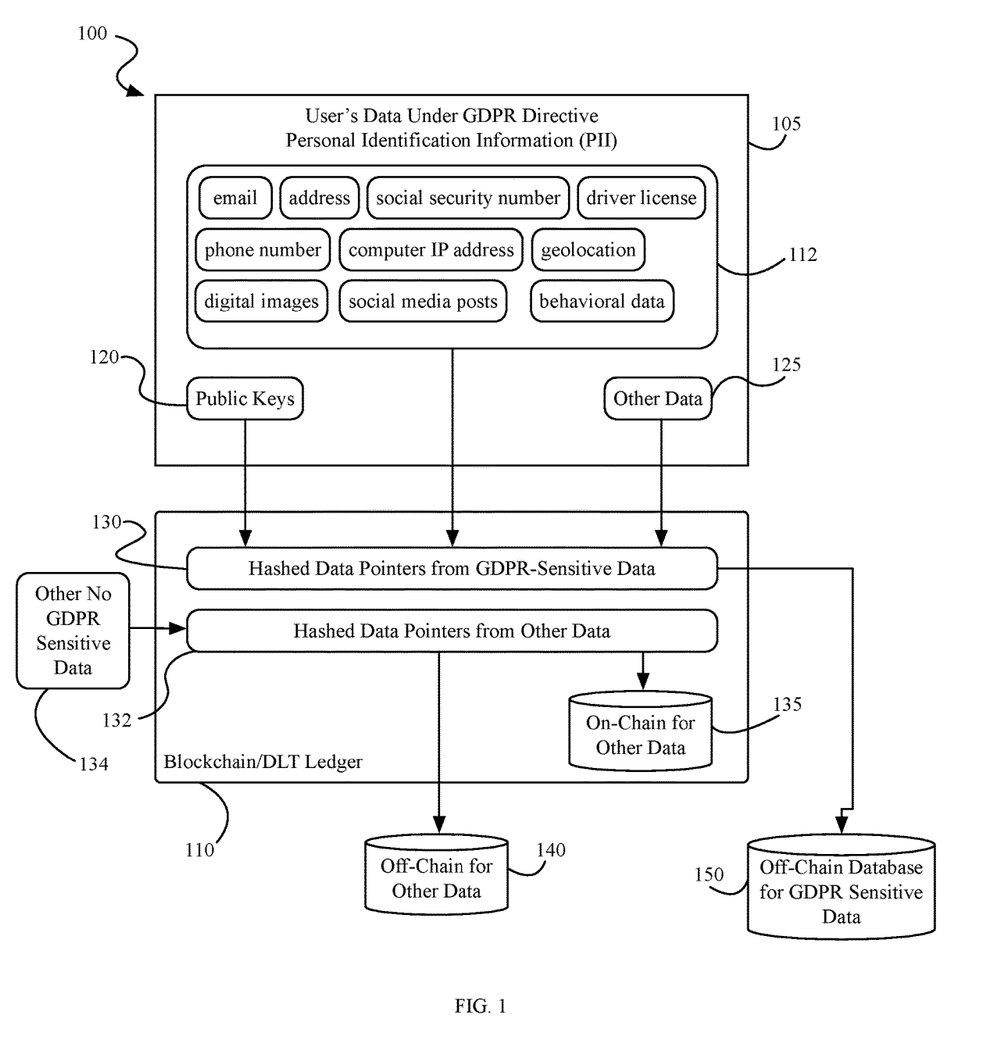
FIG. 1 is a block diagram schematically a GDPR-Blockchain compliant architecture, in accordance with an embodiment of the present invention.

With reference to FIG. 1, the present invention provides a GDPR-Blockchain Compliant Architecture 100 comprising a blockchain or distributed ledger technology (DLT) 110 and one or more off-chain databases 150. User data under GDPR directive 105, such as PII 112, which may include email addresses, social security number, social media posts, etc., are provided by the user. Hashed data pointers 130 are generated for the GDPR sensitive data, which are then stored in the blockchain ledger 110. Hashed data pointers 130 for public keys 120 and other data 125 may additionally be stored in the blockchain ledger 110. Hashed data pointers 132 from data, other than the user's data 105, such as other non-GDPR sensitive data 134, may additionally be stored in the blockchain ledger 110. Both off-chain 140 and on-chain databases 135 may be used to store the hashed values 132 for the data other than the GDPR sensitive data.

In the present invention, in order to comply with the GDPR "right to be forgotten", the GDPR-Blockchain Compliant architecture 100 further includes an off-chain or cloud database for the GDPR sensitive data 150. The use of the off-chain database 150 for the storage of the hashed values of the GDPR sensitive data 130 in accordance with the present invention to ensure GDPR compliance is described in further detail below.

The present invention provides a system and method employing a new family of hash functions that obviates instantiation of data between source and destination by structuring a proof algorithm that results in a new GDPR-PII Hash value "X-Proved". The resulting hash value does not include information on the original data.

In the present intention, a new value of "X-Proved GDPR Compliant" message is generated where "hash" is outside the data block itself and is triggered by an event of "z" to prove GDPR compliance. The use of hashing functions are foundational to the inventive method, but only in the development of a new value of "X-Proved GDPR Compliant" message which could be posted to the blockchain, wherein the resulting value is no longer related to the original data value, thereby complying with GDPR regulations.

In various embodiments, the present invention provides a system and method for referencing personal data in a blockchain ledger without being able to draw conclusions on the data itself. The inventive concept is achieved by applying a family of hash functions h_s to the message m such that for any given hash value v and message m there is a function h_s in the family which, when applied to m gives exactly the value v.

In one embodiment, in a first step of the present invention, message m is hashed to the value v=h_s(m) and v is stored in the blockchain ledger and s and m are stored outside the blockchain ledger (off-chain). In a next step, if m needs to be deleted upon request, then an arbitrary pseudonym m' is selected to calculate a new s' to obtain the same hash v=s'm'. At a next step, m and s are deleted from the off-chain database and replaced with m', s', thereby resulting in a proper anonymization while still providing the correct reference.

In another embodiment, the method may begin when an enterprise or service provider triggers the GDPR proof of compliance process. In response to the trigger, the method proceeds to iterate pre-hash proof states as part of the hash process, wherein a value of t can be inserted for time=milliseconds. When the hash process has completed, GDPR-Hash Value "X-Proved GDPR Compliant Message", wherein X can be an arbitrary numerical value, can be generated. This value-proof can then be sequentially time-stamped based on t and posted on a public blockchain ledger. Exemplary embodiments for generating the "X-Proved GDPR Compliant Message" are described in the following paragraphs.

In an exemplary embodiment for calculating a new s' to obtain the same hash, multiplication in a finite field K may be performed. Herein, let m, v and s be simply represented by elements of the field K. The mapping h_s: K--->K is given by m is mapped to v=ms. If v, m is given, s=v/m results.

In a specific embodiment, the method of the present invention may include:
1. Select a prime number p and a primitive root g mod p. Both can be made public.
2. Let the privacy information (message) be represented by a residue m mod p and freely select another residue s mod p. Both, the residues of m and s are stored outside of the blockchain ledger (off-chain). The blockchain ledger just stores the residue v=ms mod p.
3. If a request is received to delete the residue of m (outside the ledger), an arbitrary new substitute $m_{new}$ mod p is chosen and $s_{new}:=vm_{new}$ mod p is calculated and m outside the ledger is replaced by $m_{new}$ and s by $s_{new}$. Then, $m_{new} \cdot s_{new} = ms = v \mod p$, and m, s are then deleted from the off-chain database.

In a specific exemplary embodiment of the above described method of the present invention:
1. Assuming, p=29 and g=10.
2. Let the privacy information be represented by $m \equiv 13 \equiv 10^2 \mod 29$. Then s is arbitrarily chosen to be $s \equiv 24 \equiv 10^4 \mod 29$ and $ms \equiv g^6 \equiv 22 \mod 29$ is stored in the blockchain ledger.
3. When removal of data is requested, m≡13 is replaced by an arbitrary value $m_{new}$, say $m_{new} \equiv 17$, then $s_{new} \equiv vm_{new}^{-1} \equiv g^{27} \equiv 3 \mod 29$ is calculated and 13, 24 are deleted from the off-chain database and replaced by 17, 3.

Figure 2:
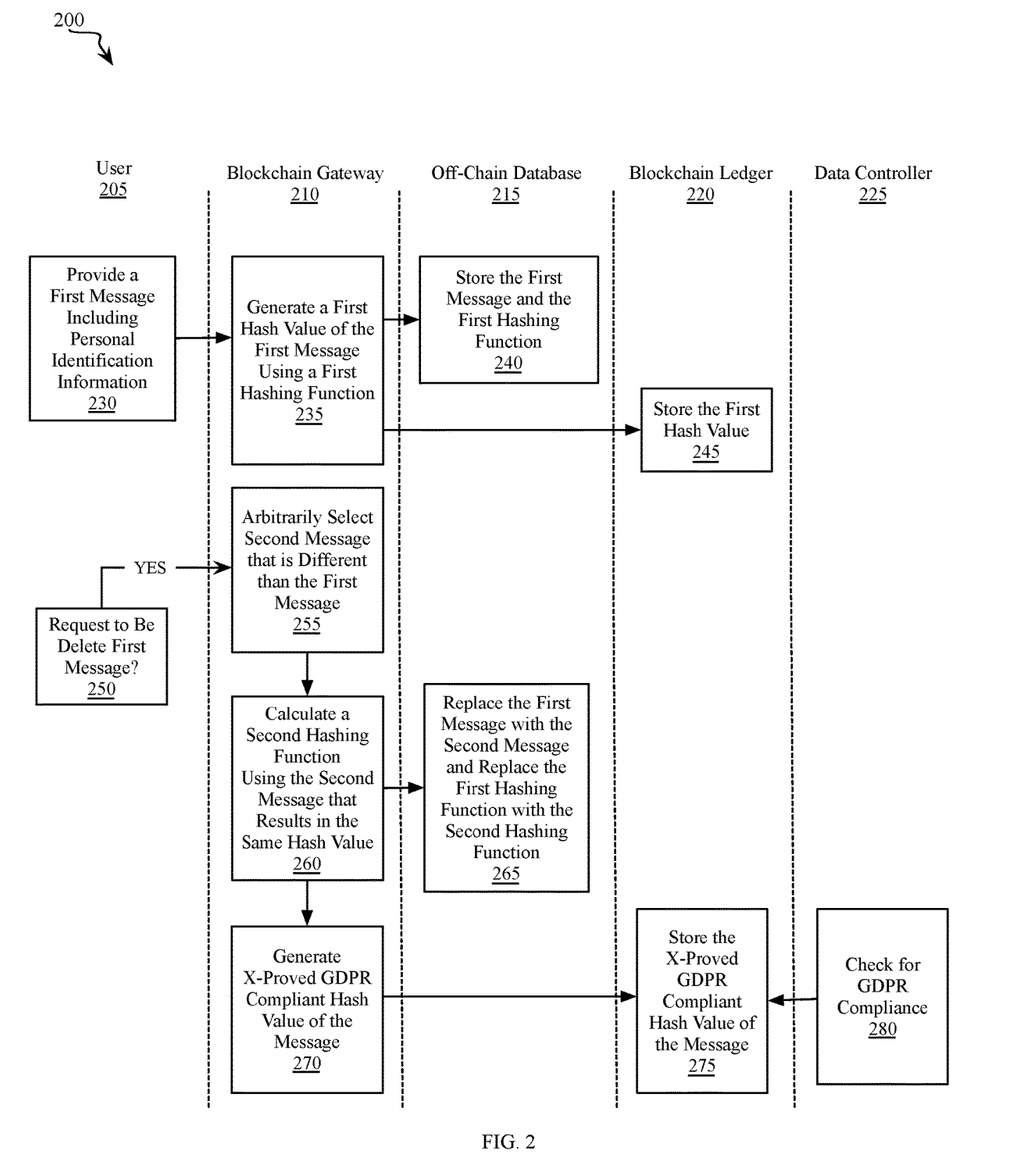
FIG. 2 is swim diagram illustrating a method for providing GDPR blockchain hashing compliance, in accordance with an embodiment of the present invention.

FIG. 2 illustrates a swim diagram of an exemplary process 200 for providing GDPR blockchain hashing compliance, in accordance with an embodiment of the present invention. For example, the process 200 can be implemented using a blockchain gateway device 210, controlled by a user 205, to store messages and hashing functions in an off-chain database 215 and to store hashed values in a blockchain ledger 220. The process 200 provides GDPR compliance when queried by a data controller 225.

In operation, a user 205 of the GDPR compliant blockchain system 200 provides a first message including personal identity information (PII) to a blockchain gateway 210. The blockchain gateway 210 then generates a hash value of the first message using a first hashing function 235 and then stores the hash value in the off-chain database 215. The hash value is also stored 245 in the blockchain ledger 220. The user 205 may be providing their PII to a data controller 225 to be used for verification of the user's identity, however no PII is stored in the blockchain ledger 220.

In order to comply with GDPR requirements, "The Right to Be Forgotten" must be adhered to by the blockchain gateway 210, wherein the blockchain gateway 210 must guarantee that the stored hash value cannot to attributed to user data. As such, when the blockchain gateway 220 receives a request to delete the first message, the blockchain gateway 220 arbitrarily selects a second message that is different than the first message 255. The blockchain gateway 220 then calculates a second hashing function using the second message that results in the same hash value 260. The blockchain gateway then replaces the first message with the second message and replaces the first hashing function with the second hashing function 265 in the off-chain database 215. In response, an X-proved GDPR compliant hash value of the message is generated 270 by the blockchain gateway 210, which is then stored 275 in the blockchain ledger 220. When the data controller 225 checks for GDPR compliance 280 with the execution of the right to be forgotten requested by the user 205, the X-proved GDPR compliant message 275 is provided to the data controller 225, thereby verifying GDPR compliant anonymization while still referencing the same hash value.

Figure 3:
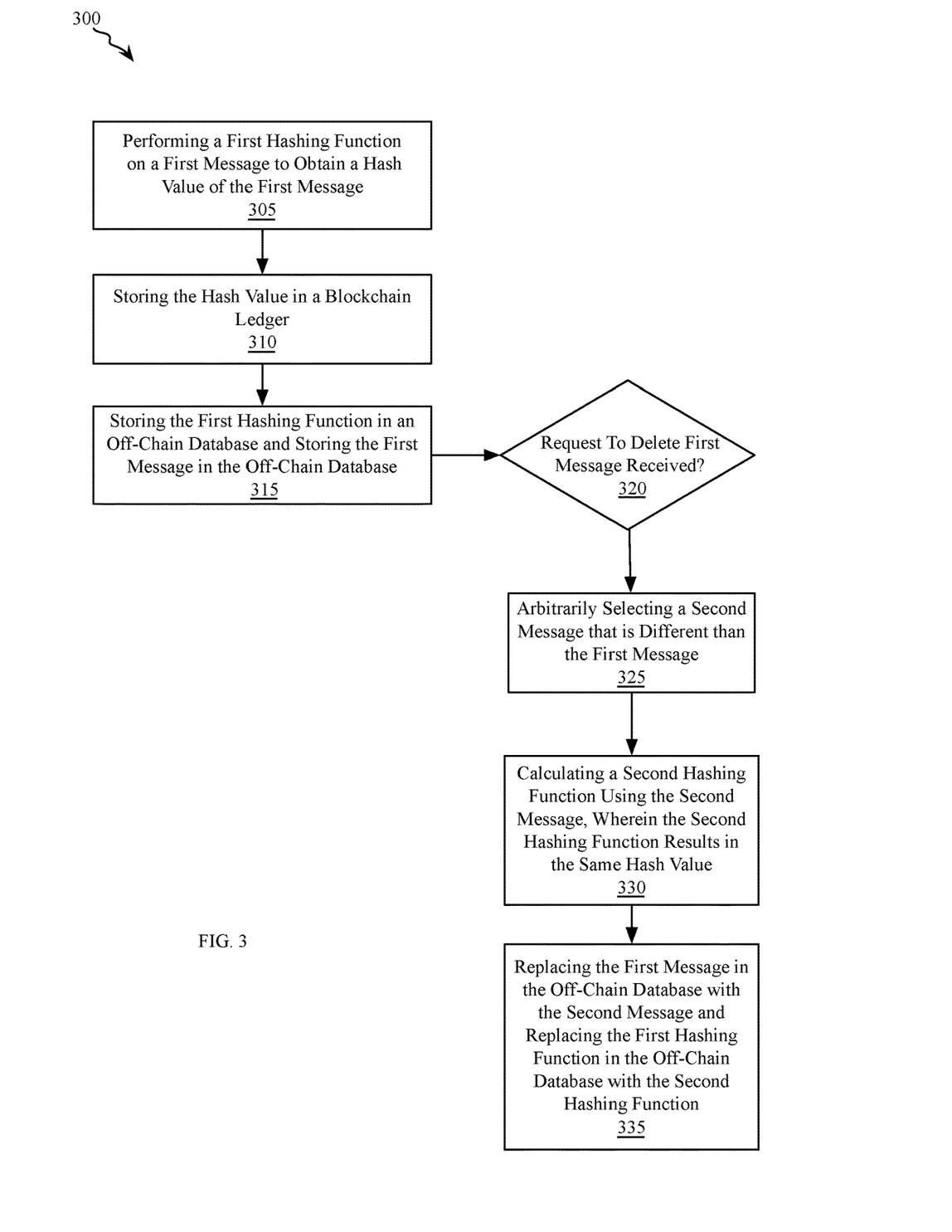
FIG. 3 is a flow diagram illustrating a method for providing GDPR blockchain compliance, in accordance with an embodiment of the present invention.

FIG. 3 illustrates a computer implemented method 300 for providing general data protection regulation (GDPR) compliant hashing in blockchain ledgers in accordance with the present invention. Step 305 includes, performing a hashing function on a first message to obtain a hash value of the first message. At step 310, the hash value is stored in the blockchain ledger and at step 315, the first hashing function and the first message are stored in the off-chain database. At step 320, upon receiving a request to delete the first message from the blockchain ledger, the method continues at step 325 by arbitrarily selecting a second message. At step 330, the method continues by calculating a second hashing function using the second message, wherein the second hashing function results in the same hash value. At step 335 the first message in the off-chain database is replaced by the second message and the first hashing function in the off-chain database is replaced by the second hashing function, thereby providing GDPR compliant anonymization while still referencing the same hash value.

As such, in various embodiments, the present invention provides a system a method for automatically ensuring GDPR compliance when utilizing blockchain technology. While the inventive concept has been described based upon GDPR compliance, this is not intended to be limiting and compliance with various other data regulations are within the scope of the present invention.

Figure 4:
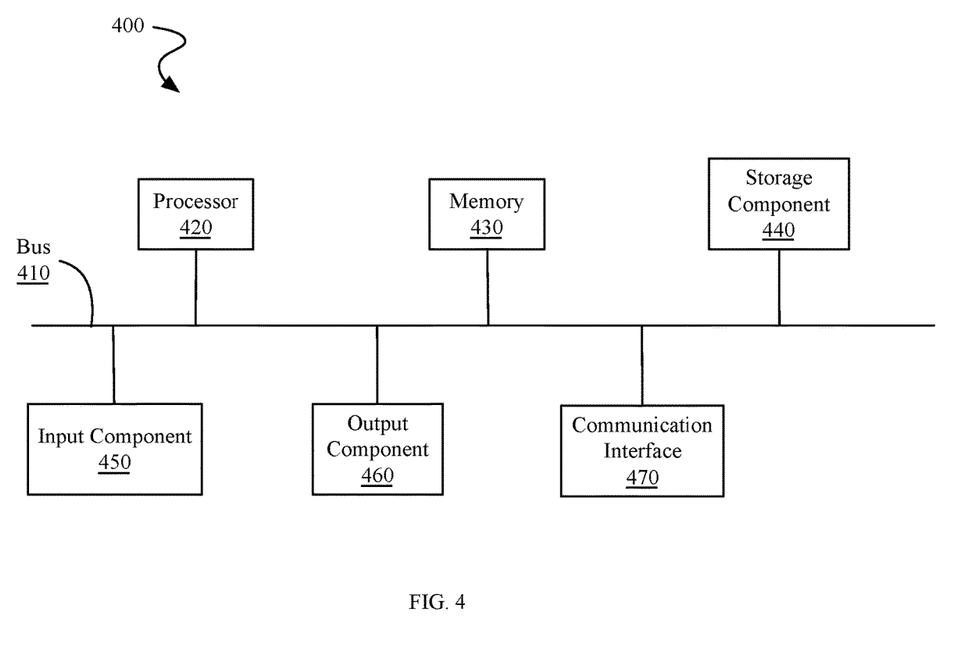
FIG. 4 is a block diagram illustrating the components of a GDPR blockchain gateway device, in accordance with an embodiment of the present invention.

FIG. 4 is a block diagram 400 illustrating the components of an exemplary blockchain gateway device, in accordance with the present invention. As shown in FIG. 4, the blockchain gateway device includes a processor 420 and one or more memory devices 430 storing computer-executable instructions that, when executed with the processor, cause the system to at least, receive a first message from a user, wherein the first message comprises personal identification information (PII) and perform a first hashing function on the first message to obtain a hash value of the first message. The processor 420 is further configured to store the hash value of the first message in a blockchain ledger, store the first hashing function in an off-chain database and store the first message in the off-chain database. The processor 420 is further configured to receive a request to be forgotten from the user, arbitrarily select a second message that is different than the first message, calculate a second hashing function using the second message, wherein the second hashing function results in the same hash value, replace the first message in the off-chain database with the second message, replace the first hashing function in the off-chain database with the second hashing function and store a GDPR compliant hash value of the message in the blockchain ledger.

In some implementations, a blockchain gateway device 400 for implementing the GDPR-blockchain compliant architecture shown in FIG. 1, may include one or more the components of the blockchain gateway device 400. As shown in FIG. 4, the blockchain gateway device 400 may include a bus 410, a processor 420, a memory 430, a storage component 440, an input component 450, an output component 460, and a communication interface 470.

Bus 410 may include circuitry that permits communication among the components of the blockchain gateway device 400. Processor 420 may be implemented in hardware, firmware, or a combination of hardware and software. Processor 420 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 420 includes one or more processors capable of being programmed to perform a function. Memory 430 may include a random-access memory (RAM), a read only memory (ROM), and/or another type of dynamic or static storage device (e.g., a flash memory, a magnetic memory, and/or an optical memory) that stores information and/or instructions for use by processor 420.

Storage component 440 may be configured for storing information and/or software related to the operation and use of the blockchain gateway device 400. For example, storage component 440 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 450 may include circuitry that allows the blockchain gateway device 400 to receive information, such as via user input, such as, a touch screen display, a keyboard, a keypad, a mouse, a button, a switch, and/or a microphone. Output component 460 may include a component that provides output information from the blockchain gateway device 400, such as a display or a speaker.

Communication interface 470 may include a transceiver circuitry that allows the blockchain gateway device 400 to communicate with other devices, such as via a wired connection, a wireless connection, or a combination of wired and wireless connections. Communication interface 470 may allow device 400 to receive information from another device and/or provide information to another device. For example, communication interface 470 may include an Ethernet interface, an optical interface, a coaxial interface, an infrared interface, a radio frequency (RF) interface, a universal serial bus (USB) interface, a Wi-Fi interface, a cellular network interface, and/or the like.

The blockchain gateway device 400 may perform one or more processes described herein. The blockchain gateway device 400 may perform these processes based on the processor 420 executing software instructions stored by a non-transitory computer-readable medium, such as a memory 430 and/or storage component 440.

The specific arrangement of components shown in FIG. 4 are provided as an exemplary embodiment. In practice, the blockchain gateway device 400 may include additional components, fewer components, different components, or differently arranged components than those illustrated in FIG. 4.

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While methods, apparatuses, and systems have been described in connection with exemplary embodiments of the various figures, it is to be understood that other similar embodiments can be used or modifications and additions can be made to the described embodiments for performing the same function without deviating therefrom. Therefore, the invention should not be limited to any single embodiment, but rather should be construed in breadth and scope in accordance with the appended claims.

What is claimed is:

1. A computer implemented method for providing general data protection regulation (GDPR) compliant hashing in blockchain ledgers, the method comprising:
    receiving a first message from a user at a blockchain gateway device, wherein the first message comprises personal identification information (PII);
    performing, at the blockchain gateway device, a first hashing function on the first message to obtain a hash value of the first message;
    storing the hash value of the first message in a blockchain ledger;
    storing the first hashing function in an off-chain database;
    storing the first message in the off-chain databases
    receiving, at the blockchain gateway device, a request to delete the first message;
    arbitrarily selecting a second message that is different than the first message;
    calculating a second hashing function using the second message, wherein the second hashing function results in the same hash value;
    replacing the first message in the off-chain database with the second message;
    replacing the first hashing function in the off-chain database with the second hashing function; and
    storing a GDPR compliant hash value of the message in the blockchain ledger.

2. The method of claim 1, wherein the personal identification information (PII) of the user is selected from social security numbers, mailing addresses, email addresses, phone numbers, IP addresses, login IDs, social media posts, digital images, geolocation data, biometric data, and behavioral data.

3. The method of claim 1, further comprising:
    requesting, by a data controller, a GDPR proof of compliance to the blockchain gateway device; and
    providing the GDPR compliant message to the data controller in response to the request.

4. The method of claim 1, wherein the GDPR compliant message comprises a timestamp.

5. The method of claim 1, wherein the first hashing function and the second hashing function comprise a selected prime number.

6. The method of claim 1, wherein performing, at the blockchain gateway device, a first hashing function on the first message to obtain a hash value of the first message further comprises:
    selecting a prime number p and a primitive root g mod p;
    letting the first message be represented by a first residue m mod p;
    selecting a first hashing function as a second residue s mod p; and
    wherein storing the first message in the off-chain database comprises storing the first residue m mod p, storing the first hashing function in the off-chain database comprises storing the second residue s mod p, and storing the hash value of the first message in the blockchain ledger comprises storing the third residue $v \equiv ms$ mod p.

7. The method of claim 6, further comprising:
    wherein receiving the request to delete the first message comprises a request to delete the first residue of m;
    wherein arbitrarily selecting a second message that is different than the first message further comprises selecting $m_{new}$ mod p;
    wherein calculating a second hashing function using the second message, wherein the second hashing function results in the same hash value further comprises calculating $s_{new} \equiv v m_{new}^{-1}$ mod p; and
    wherein replacing the first message in the off-chain database with the second message further comprises replacing m in the off-chain database with $m_{new}$;
    wherein replacing the first hashing function in the off-chain database with the second hashing function further comprises replacing s with $s_{new}$.

8. The method of claim 6, wherein the prime number p and the primitive root g mod p can both be made public.

9. A blockchain gateway device for providing general data protection regulation (GDPR) compliant hashing in blockchain ledgers, the system comprising:
    a processor; and
    one or more memory devices storing computer-executable instructions that, when executed with the processor, cause the system to at least:
        receive a first message from a user, wherein the first message comprises personal identification information (PII);
        perform a first hashing function on the first message to obtain a hash value of the first message;
        store the hash value of the first message in a blockchain ledger;
        store the first hashing function in an off-chain database;
        store the first message in the off-chain database;
        receive a request to delete the first message;
        arbitrarily select a second message that is different than the first message;
        calculate a second hashing function using the second message, wherein the second hashing function results in the same hash value;
        replace the first message in the off-chain database with the second message;
        replace the first hashing function in the off-chain database with the second hashing function; and
        store a GDPR compliant hash value of the message in the blockchain ledger.

10. The system of claim 9, wherein the personal identification information (PII) of the user is selected from social security numbers, mailing addresses, email addresses, phone numbers, IP addresses, login IDs, social media posts, digital images, geolocation data, biometric data, and behavioral data.

11. The system of claim 9, wherein the one or more memory devices storing computer-executable instructions that, when executed with the processor, cause the system to further:
    receive a request from a data controller for GDPR proof of compliance; and
    provide the GDPR compliant message to the data controller in response to the request.

12. The system of claim 9, wherein the GDPR compliant message comprises a timestamp.

13. The system of claim 9, wherein the first hashing function and the second hashing function comprise a selected prime number.

14. The system of claim 9, wherein the one or more memory devices storing computer-executable instructions that, when executed with the processor, cause the system to further perform a first hashing function on the first message to obtain a hash value of the first message further comprises computer-executable instructions to:
    select a prime number p and a primitive root g mod p;
    let the first message be represented by a first residue m mod p;

select the first hashing function as a second residue s mod p; and store the first residue m mod p as the first message;

store second residue s mod p as the first hashing function; and store third residue v≡ms mod p as the hash value.

15. The system of claim 14, wherein the one or more memory devices storing computer-executable instructions that, when executed with the processor, further comprises computer-executable instructions to:

receive a request to delete the first residue of m;

select a second message that is different than the first message as $m_{new}$ mod p;

calculate a second hashing function using the second message, wherein the second hashing function results in the same hash value, as $s_{new} \equiv vm_{new}^{-1}$ mod p; and replace the first message in the off-chain database with the second message by replacing m in the off-chain database with $m_{new}$;

replace the first hashing function in the off-chain database with the second hashing function by replacing s with $s_{new}$.

16. The system of claim 14, wherein the prime number p and the primitive root g mod p can both be made public.

17. One or more non-transitory computer-readable media having computer-executable instructions for performing a method of running a software program on a computing device for providing general data protection regulation (GDPR) compliant hashing in blockchain ledgers, the method comprising, the computing device operating under an operating system, the method including issuing instructions from the software program comprising:

receiving a first message from a user at a blockchain gateway device, wherein the first message comprises personal identification information (PII);

performing, at the blockchain gateway device, a first hashing function on the first message to obtain a hash value of the first message;

storing the hash value of the first message in a blockchain ledger;

storing the first hashing function in an off-chain database;

storing the first message in the off-chain database receiving, at the blockchain gateway device, a request to delete the first message;

arbitrarily selecting a second message that is different than the first message;

calculating a second hashing function using the second message, wherein the second hashing function results in the same hash value;

replacing the first message in the off-chain database with the second message;

replacing the first hashing function in the off-chain database with the second hashing function; and storing a GDPR compliant hash value of the message in the blockchain ledger.

\* \* \* \* \*